US00PP35903P2

(12) United States Plant Patent
Vitten et al.

(10) Patent No.: US PP35,903 P2
(45) Date of Patent: Jul. 2, 2024

(54) RASPBERRY PLANT NAMED 'DRISRASPTWENTYFOUR'

(50) Latin Name: ***Rubus idaeus* L.**
Varietal Denomination: DrisRaspTwentyFour

(71) Applicant: Driscoll's, Inc., Watsonville, CA (US)

(72) Inventors: Matthias D. Vitten, Aptos, CA (US); Kyle Rak, Salinas, CA (US); Luis Miguel Rodriguez, Jalisco (MX); James A. Heilig, Salinas, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 18/339,905

(22) Filed: Jun. 22, 2023

(51) Int. Cl.
*A01H 5/08* (2018.01)
*A01H 6/74* (2018.01)

(52) U.S. Cl.
USPC ..... Plt./204

(58) Field of Classification Search
USPC ..... Plt./204
CPC ..... A01H 5/08; A01H 5/00; A01H 6/7499; A01H 6/74
See application file for complete search history.

(56) References Cited

U.S. PATENT DOCUMENTS

| | | | |
|---|---|---|---|
| PP4,486 | P | 11/1979 | Reiter |
| PP6,493 | P | 12/1988 | Wilhelm |
| PP7,436 | P | 2/1991 | Ackerman |
| PP7,437 | P | 2/1991 | Ackerman |
| PP7,528 | P | 5/1991 | Ackerman |
| PP8,022 | P | 11/1992 | Wilhelm |
| PP8,027 | P | 11/1992 | Wilhelm |
| PP9,340 | P | 10/1995 | Wilhelm et al. |
| PP9,653 | P | 10/1996 | Wilhelm et al. |
| PP9,696 | P | 11/1996 | Fear |
| PP11,067 | P | 9/1999 | Fear et al. |
| PP11,087 | P | 10/1999 | Fear et al. |
| PP11,094 | P | 10/1999 | Fear et al. |
| PP11,102 | P | 10/1999 | Fear et al. |
| PP14,761 | P2 | 5/2004 | Fear et al. |
| PP14,781 | P2 | 5/2004 | Fear et al. |
| PP14,804 | P2 | 5/2004 | Fear et al. |
| PP14,860 | P2 | 6/2004 | Fear et al. |
| PP14,903 | P2 | 6/2004 | Fear et al. |
| PP14,904 | P2 | 6/2004 | Fear et al. |
| PP18,658 | P3 | 3/2008 | Fear et al. |
| PP18,659 | P3 | 3/2008 | Fear et al. |
| PP19,137 | P3 | 8/2008 | Harrison et al. |
| PP19,656 | P2 | 1/2009 | Hamilton et al. |
| PP22,246 | P3 | 11/2011 | Hamilton et al. |
| PP22,731 | P2 | 5/2012 | Fear et al. |
| PP23,477 | P3 | 3/2013 | Hamilton et al. |
| PP24,610 | P3 | 7/2014 | Hamilton et al. |
| PP25,044 | P3 | 11/2014 | Hamilton et al. |
| PP25,045 | P3 * | 11/2014 | Hamilton ..... A01H 5/08 Plt./204 |
| PP27,644 | P3 | 2/2017 | Hamilton et al. |
| PP28,775 | P2 | 12/2017 | Hamilton et al. |
| PP28,856 | P3 | 1/2018 | Hamilton et al. |
| PP29,402 | P2 | 6/2018 | Vitten et al. |
| PP30,577 | P2 | 6/2019 | Vitten et al. |
| PP30,733 | P2 | 7/2019 | Hamilton et al. |
| PP31,850 | P2 | 6/2020 | Hamilton et al. |
| PP32,496 | P2 | 11/2020 | Vitten et al. |
| PP32,722 | P2 | 1/2021 | Vitten et al. |
| PP33,723 | P2 | 12/2021 | Vitten et al. |
| PP33,736 | P2 | 12/2021 | Vitten et al. |
| PP33,758 | P2 | 12/2021 | Vitten et al. |
| PP34,070 | P2 | 3/2022 | Vitten et al. |

OTHER PUBLICATIONS

Cousineau et al. (1992). "Use of Isoenzyme Analysis to Characterize Raspberry Cultivars and Detect Cultivar Mislabeling," HortScience, 27(9):1023-1025.
Williams et al. (1990). "DNA polymorphisms amplified by arbitrary primers are useful as genetic markers," Nucleic Acids Research, 18(22):6531-6535.

* cited by examiner

*Primary Examiner* — June Hwu
(74) *Attorney, Agent, or Firm* — Morrison & Foerster LLP

(57) ABSTRACT

A new and distinct variety of raspberry plant named 'DrisRaspTwentyFour', particularly selected for the flavor, texture, and firmness of its fruit, is disclosed.

4 Drawing Sheets

Latin name:
Botanical classification: *Rubus idaeus* L.
Varietal denomination: The varietal denomination of the claimed variety of raspberry plant is 'DrisRaspTwentyFour'.

BACKGROUND OF THE INVENTION

Raspberries are the edible fruit of a multitude of plant species in the genus *Rubus* of the rose family. Most raspberry species are in the subgenus *Idaeobatus*. Raspberry plants are perennial plants with woody stems. Many of the most important modern commercial red raspberry cultivars derive from hybrids between *R. idaeus* and *R. strigosus*. Recent breeding has resulted in cultivars that are thornless and more strongly upright, not needing staking.

Both the red and the black raspberry species have albino-like pale-yellow natural or horticultural variants. Fruits from such plants are called golden raspberries or yellow raspberries. Most pale-fruited raspberries commercially sold in the eastern United States are derivatives of red raspberries. Yellow-fruited variants of the black raspberry are sometimes grown in home gardens. Despite their dissimilar appearance, golden raspberries retain the distinctive flavor of their respective red or black species.

An individual raspberry fruit is made up of around 100 drupelets, each of which contains a juicy pulp and a single central seed. A raspberry bush can yield several hundred berries a year. Unlike blackberries and dewberries, a raspberry has a hollow core once it is removed from the receptacle.

Raspberries are traditionally planted in the winter as dormant canes, but planting plugs produced by tissue culture is also common. Additionally, the long cane production method consists of growing canes for one year in cold climates where the bud break is early, and then transplanting the canes to warm climates where they quickly flower and can produce an early season crop. A very vigorous crop, raspberries spread well and can be considered invasive, using extended underground shoots (also known as suckers or basal shoots) that can develop roots and individual plants.

Raspberries are a popular fruit that are recognized for their antioxidants, high fiber, and as a good source of vitamin C. Raspberry fruit is typically consumed as fresh fruit, individually quick frozen (IQF) fruit, or in prepared foods, such as purées, juices, jellies, jams, grocery items, baked goods, and snack foods.

Raspberry is an important and valuable commercial fruit crop, widely grown in all temperate regions of the world. Accordingly, there is a need for new varieties of raspberry plant. In particular, there is a need for improved varieties of raspberry plant that are stable, high yielding, and agronomically sound.

SUMMARY OF THE INVENTION

In order to meet these needs, the present invention is directed to an improved variety of raspberry plant. In particular, the invention relates to a new and distinct variety of raspberry plant (*Rubes idaeus* L.), which has been denominated as 'DrisRaspTwentyFour'.

Raspberry plant variety 'DrisRaspTwentyFour' was selected in Santa Cruz County, California in June of 2017 and originated from a cross between the proprietary female parent 'RH761.1' (unpatented) and the proprietary male parent 'RJ0750.2' (unpatented). The original seedling of the new variety was first asexually propagated in Santa Cruz County, California via root cuttings in October 2018.

'DrisRaspTwentyFour' was subsequently asexually propagated via root cuttings, and has undergone testing in Santa Cruz County, California for five years (2018 to 2023). The present variety has been found to be stable and reproduce true to type through successive asexual propagations via root cuttings and tissue culture.

'DrisRaspTwentyFour' was particularly selected for the flavor, texture, and firmness of its fruit.

BRIEF DESCRIPTION OF THE DRAWINGS

This new raspberry plant is illustrated by the accompanying photographs. The colors shown are as true as can be reasonably obtained by conventional photographic procedures. The photographs are of plants that are two years old.

DETAILED BOTANICAL DESCRIPTION

Figure 1:
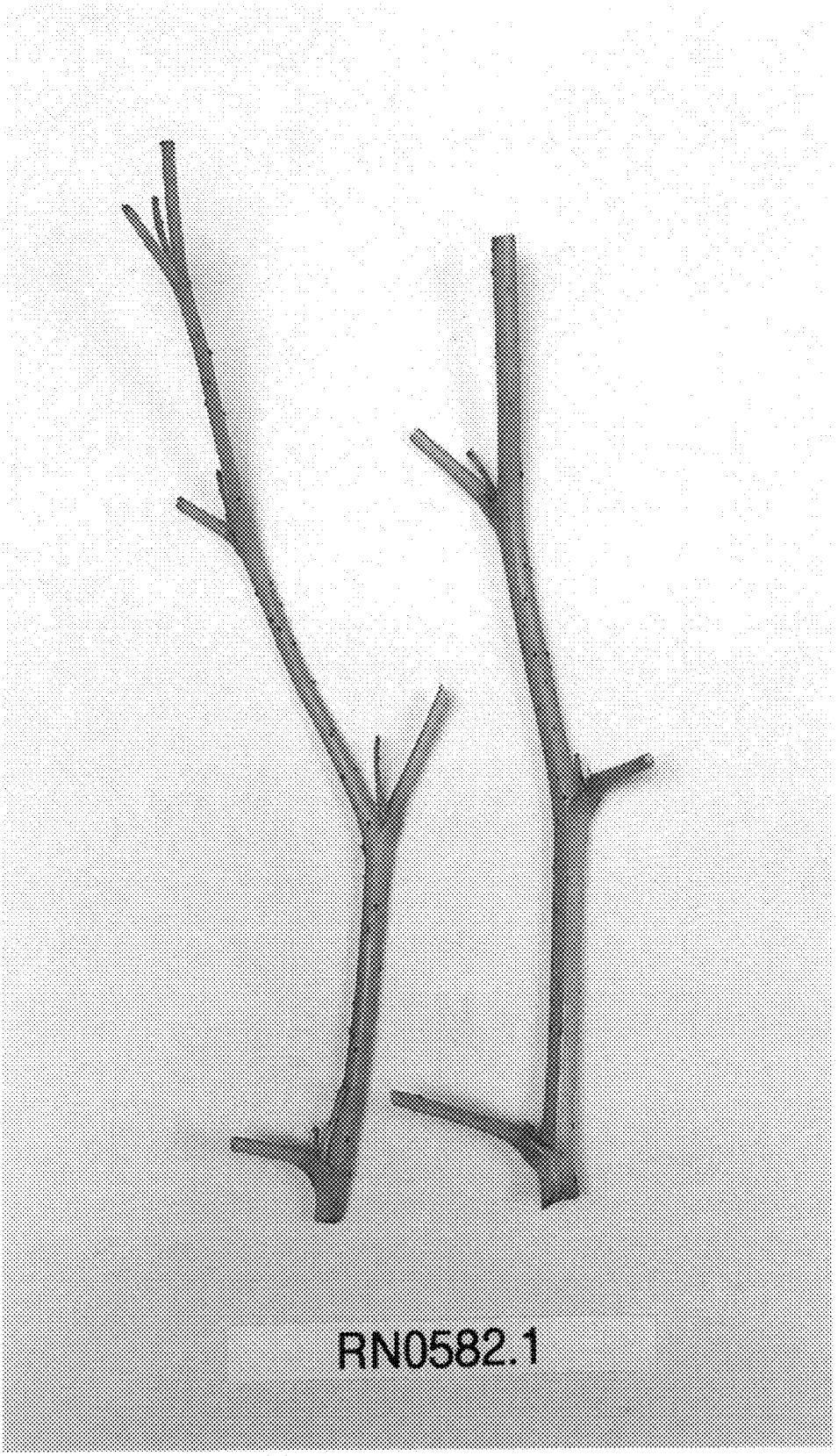
FIG. 1 illustrates sections of primocanes of raspberry variety 'DrisRaspTwentyFour' (labeled with its breeder's reference code 'RN0582.1').
Figure 2:
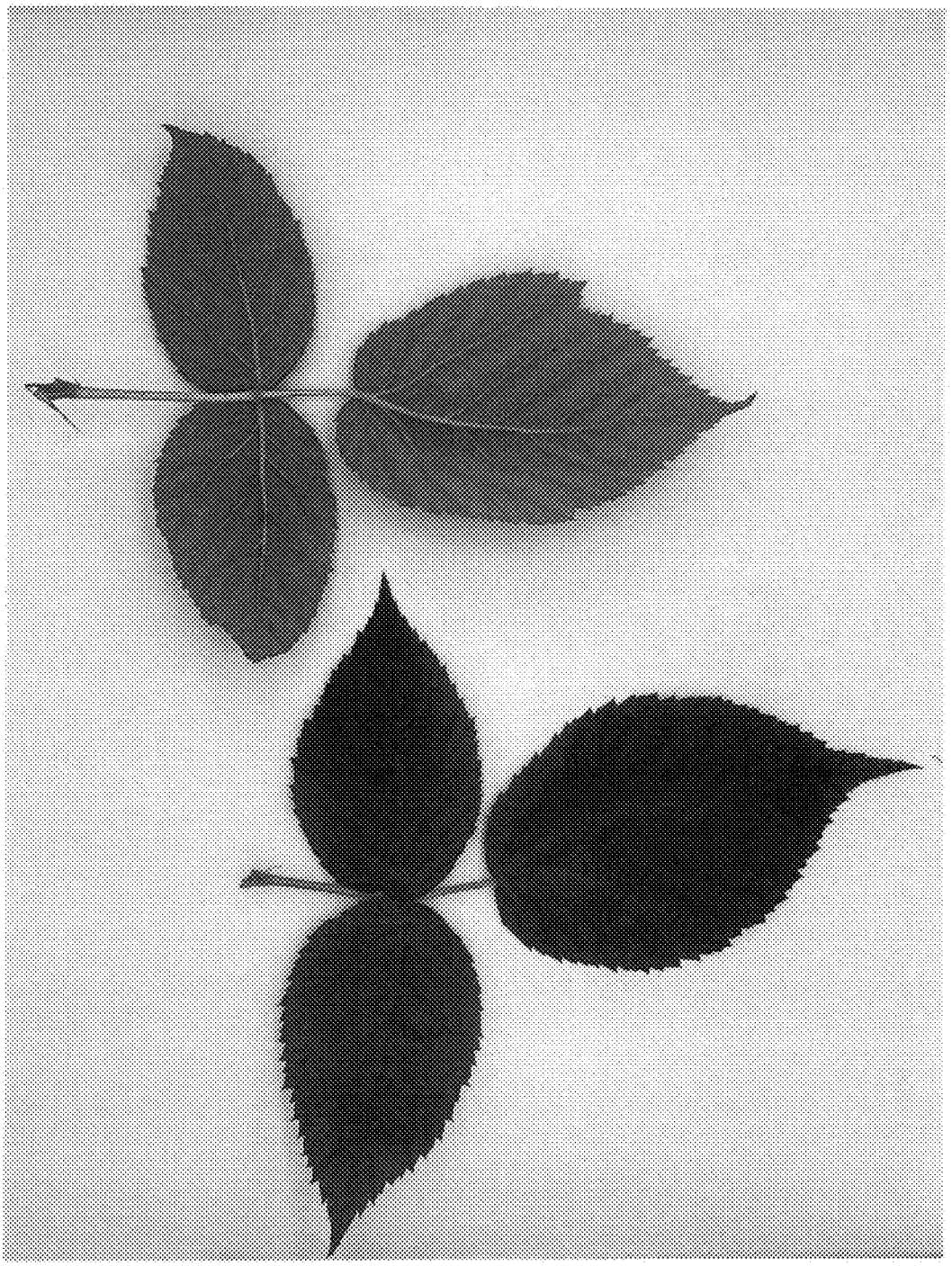
FIG. 2 illustrates the upper surface (left leaf) and the lower surface (right leaf) of leaves of raspberry variety 'DrisRaspTwentyFour'.
Figure 3:
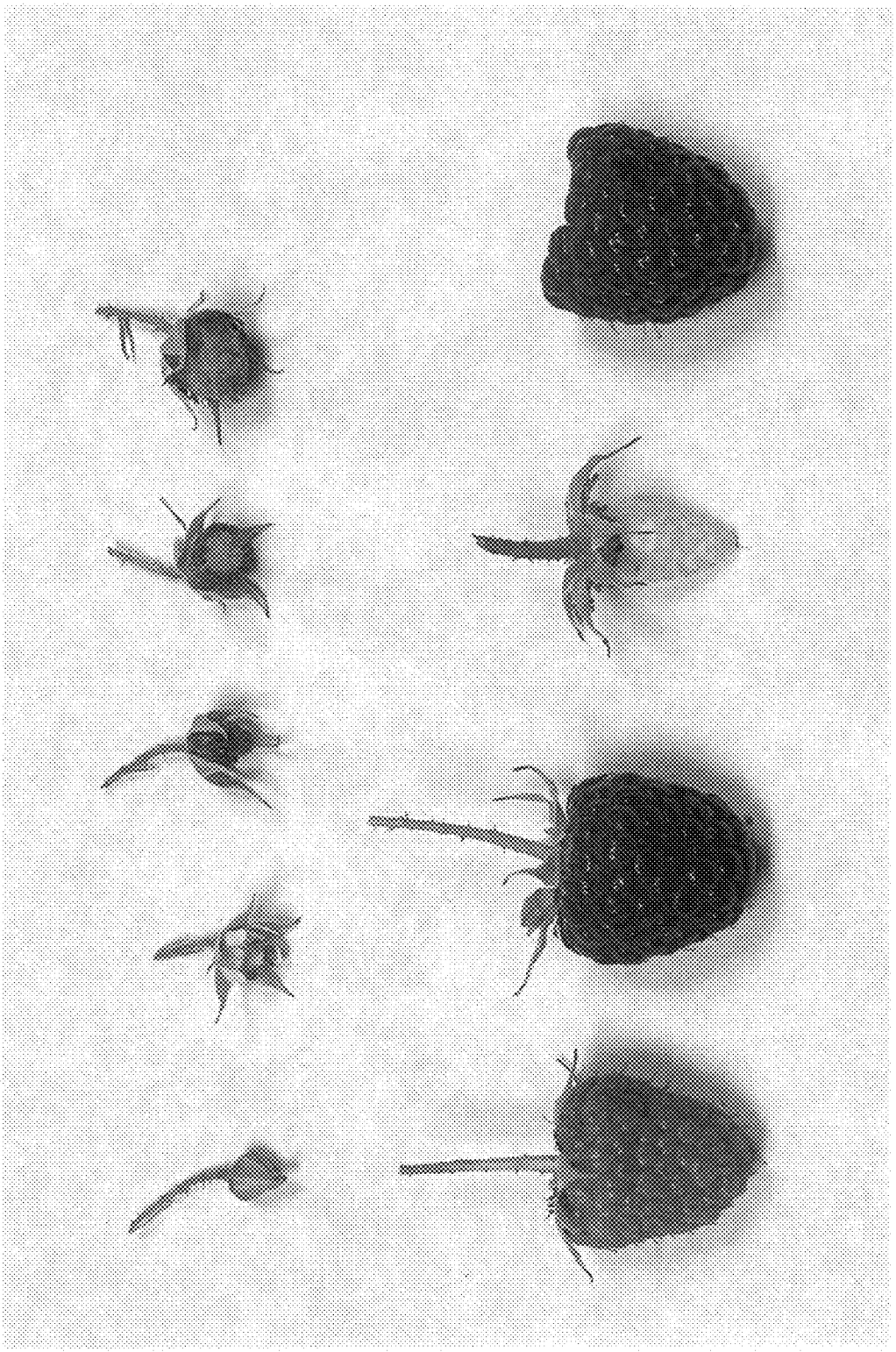
FIG. 3 illustrates flowers and fruit of raspberry variety 'DrisRaspTwentyFour' at various stages of development.
Figure 4:
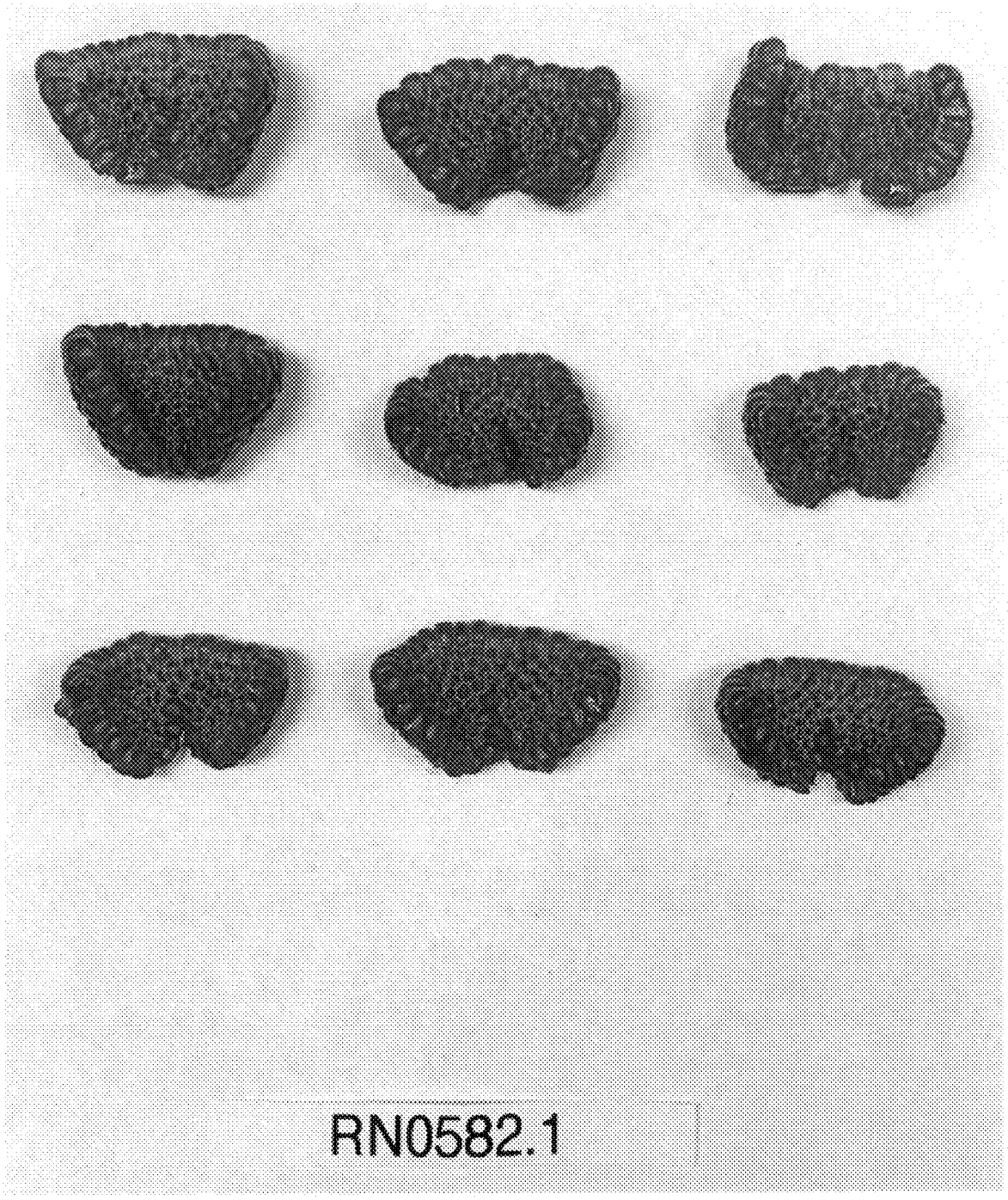
FIG. 4 illustrates longitudinal sections displaying the inner surface of fruit of raspberry variety 'DrisRaspTwentyFour' (labeled with its breeder's reference code 'RN0582.1').

The following descriptions set forth the distinctive characteristics of 'DrisRaspTwentyFour'. Unless where otherwise noted, the data that define these characteristics are based on observations taken from 'DrisRaspTwentyFour' plants that were two years old, grown in Santa Cruz County, California from 2018 to 2023. These descriptions are in accordance with UPOV terminology. Color designations, color descriptions, and other phenotypical descriptions may deviate from the stated values and descriptions depending upon variation in environmental, seasonal, climatic and cultural conditions. 'DrisRaspTwentyFour' has not been observed under all possible environmental conditions. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Rosaceae.

*Botanical*.—*Rubes idaeus* L.

*Common name*.—Raspberry.

*Variety name*.—'DrisRaspTwentyFour'.

Parentage:

*Female parent*.—'RH761.1' (unpatented).

*Male parent*.—'RJ0750.2' (unpatented).

Plant:

*Height*.—217 cm.

*Width*.—160 cm.

*Length/width ratio*.—1.35.

*Cane diameter*.—1.1 cm.

*Growth habit*.—Semi-upright.

*Self-fruitness*.—Self-fruitful.

*Primocane* (*current year's cane*).—Cane length in autumn: 238 cm. Internodal distance at central ⅓ of cane: 4.840 cm. Vegetative bud length at central ⅓ of cane: 5.24 mm. Number of primocanes: 140-160 in a plot of 20 ft. Anthocyanin coloration of cane: Absent or very weak. Cane color: RHS 140A (Vivid yellowish green). Cane bloom: Medium. Shape of cane in cross-section: Rounded. Pubescence: Absent. Time of cane emergence: Medium.

*Very young shoot*.—Anthocyanin coloration of apex during rapid growth: Absent.

*Floricane* (*previous year's cane*).—Time of vegetative bud burst: Medium. Dormant cane length: 237.2 cm. Dormant cane color: RHS 199A (Moderate olive brown). Fruiting lateral attitude: Semi-erect.

*Prickles* (*spines*).—Presence: Present on peduncle, pedicel, floricane, and primocane. Density: Medium. Diameter (at base): 1.02 mm. Length (from base to tip): 0.79 mm. Color: RHS NI87A (Dark purplish grey). Attitude of tip: Upward. Presence and distribution on petioles: Present and regularly distributed.

Leaves:

*Predominant number of leaflets*.—Equally three and five.

*Profile of leaflets in cross section.*—Straight.
*Leaf rugosity.*—Weak.
*Color of upper side.*—RHS 143A (Strong yellow green).
*Color of lower side.*—RHS N138C (Pale green).
*Glossiness.*—Weak.
*Arrangement.*—Opposite.
*Terminal leaflet.*—Length: 13.13 cm. Width: 7.79 cm. Length/width ratio: 1.69. Overall shape: Ovate. Shape of apex: Acuminate. Shape of base: Cuneate. Margin: Serrate.
*Lateral leaflets.*—Length: 12.24 cm. Width: 7.8 mm. Length/width ratio: 1.57. Length to stalklet: 1.69 mm. Relative position of lateral leaflets: Touching. Overall shape: Ovate. Shape of base: Obtuse. Margin: Serrate.
*Rachis length between terminal leaflet and adjacent lateral leaflets.*—39.44 mm.
*Petiole.*—Length: 83.84 mm. Diameter: 4.22 mm. Color: RHS 144C (Strong yellow green).
*Stipule.*—Orientation: Erect.

Flowers:
*Percent of cane flowering on primocanes.*—55%.
*Diameter.*—18.24 mm.
*Petal.*—Length: 7.42 mm. Width: 3.87 mm. Length/width ratio: 1.91. Color: RHS NN155C (White).
*Pedicel.*—Length: 46.99 mm. Diameter: 1.25 mm. Number of spines on pedicel: 41. Color: RHS 144C (Strong yellow green). Anthocyanin coloration: Absent.
*Peduncle.*—Length: 31.40 mm. Diameter: 1.88 mm. Color: RHS 140B (Brilliant yellowish green). Anthocyanin coloration: Absent.

Fruit:
*Length.*—28.27 mm.
*Diameter.*—25.39 mm.
*Length/width ratio.*—1.11.
*Weight (primocane).*—5.5 g/fruit.
*Weight (floricane).*—4.9 g/fruit.
*Sweetness/soluble solids (° brix).*—10.5.
*Titratable acidity (% as citric acid).*—11.7%.
*Length of single drupe.*—6.05 mm.
*Diameter of single drupe.*—4.87 mm.
*Average number of drupes per fruit.*—97.
*General shape in lateral view.*—Conical.
*Color.*—RHS 53A (Deep red).
*Glossiness.*—Strong.
*Firmness.*—Firm.
*Adherence to plug.*—Medium.
*Seed.*—Weight: 0.0033 g/seed.

Production:
*Main bearing type.*—Both on previous year's cane in summer (floricane) and on current year's cane in autumn (primocane).
*Primocane (current year's cane).*—Time of beginning of flowering: Late June. Time of beginning of fruit ripening: Early to mid July. Length of fruiting period: Early July to late October. Percent of yield from primocane: 60% of total yield. Yield: 18,000 kg to 25,000 kg of fruit per hectare per season from 7-month-old plants when grown in Watsonville, California.
*Floricane (previous year's cane).*—Time of beginning of flowering: Late April. Time of beginning of fruit ripening: Early to mid May. Length of fruiting period: Early May to late June. Yield: 19,000 kg to 23,000 kg of fruit per hectare per season from 12-month-old plants when grown in Watsonville, California.
*Market use of fruit.*—Fresh market.
*Shipping and storage characteristics.*—Following harvest, fruit can be shipped and stored for 10 days if maintained under cooled temperatures that are standard for raspberry storage.
*Hardiness zone (heat/cold tolerance).*—Zones 4 through 8, preferring cool climates.

Resistance to diseases, pests, and abiotic stress: Not observed to date.

COMPARISONS TO PARENTAL AND REFERENCE RASPBERRY VARIETIES

'DrisRaspTwentyFour' differs from the proprietary female parent 'RH761.1' (unpatented) in that 'DrisRaspTwentyFour' has a lighter red fruit color as compared to fruit of female parent 'RH761.1'.

'DrisRaspTwentyFour' differs from the proprietary male parent 'RJ0750.2' (unpatented) in that 'DrisRaspTwentyFour' has a pleasant and sweeter fruit taste as compared to male parent 'RJ0750.2'. Fruit of 'DrisRaspTwentyFour' is also a lighter color after post-harvest as compared to fruit of male parent 'RJ0750.2', which is darker in color after post-harvest.

'DrisRaspTwentyFour' differs from reference raspberry variety 'Driscoll Maravilla' (U.S. Plant Pat. No. 14,804) in that for 'DrisRaspTwentyFour' the leaf rugosity is weak, the relative position of lateral leaflets is touching, the color of the upper side of the leaf is dark green, and the fruit glossiness is strong, whereas for 'Driscoll Maravilla' the leaf rugosity is medium, the relative position of lateral leaflets is overlapping, the color of the upper side of the leaf is medium green, and the fruit glossiness is medium.

'DrisRaspTwentyFour' differs from reference raspberry variety 'DrisRaspSeven' (U.S. Plant Pat. No. 25,045) in that for 'DrisRaspTwentyFour' the number of current season's canes is many, the leaf rugosity is weak, the number of spines on the pedicel is medium, and the fruit's adherence to the plug is medium, whereas for 'DrisRaspSeven' the number of current season's canes is few, the leaf rugosity is medium, the number of spines on the pedicel is absent or very few, and the fruit's adherence to the plug is weak.

What is claimed is:

1. A new and distinct variety of raspberry plant designated 'DrisRaspTwentyFour' as shown and described herein.

* * * * *